United States Patent [19]

Watanabe et al.

[11] Patent Number: 5,032,580

[45] Date of Patent: Jul. 16, 1991

[54] COMPSITIONS FOR ANTIVIRUS MEDICINES

[75] Inventors: Kazuhiro Watanabe; Makoto Yashiro, both of Tokyo; Makoto Machida, Tokorozawa, all of Japan

[73] Assignee: Sanyo-Kokusaku Pulp Co., Ltd., Tokyo, Japan

[21] Appl. No.: 277,311

[22] Filed: Nov. 29, 1988

[30] Foreign Application Priority Data

Dec. 28, 1987 [JP] Japan ................................ 62-332305

[51] Int. Cl.[5] ...................... A61K 27/14; A61K 31/12; C07H 15/20; C07H 15/24

[52] U.S. Cl. ...................................... 514/23; 514/685; 514/687; 514/734; 514/885; 424/195.1

[58] Field of Search ............... 424/195.1; 514/23, 885, 514/685, 687, 734

[56] References Cited

U.S. PATENT DOCUMENTS

| | | | |
|---|---|---|---|
| 4,320,225 | 3/1982 | Hashimoto et al. | 536/18.1 |
| 4,371,549 | 2/1983 | Cherukuri et al. | 426/540 |
| 4,428,876 | 1/1984 | Iwamura | 530/417 |
| 4,891,221 | 1/1990 | Shanborm | 435/2 |
| 4,898,890 | 2/1990 | Sato et al. | 514/885 |

FOREIGN PATENT DOCUMENTS

| | | |
|---|---|---|
| 259499 | 3/1988 | European Pat. Off. . |
| 48-8485 | 3/1973 | Japan . |
| 62-207212 | 9/1987 | Japan . |
| WO87/05215 | 9/1987 | World Int. Prop. O. . |

OTHER PUBLICATIONS

Sandström et al, Anti-Viral Therapy in AIDS, AIDS Press Limited, pp. 373-390, 1987.

Mitsuya et al, Retroviruses in Human Lymphoma/-Leukemia, "Protection of T Cells Against Infectivity and Cytopathic Effect of HTLV-III in Vitro", pp. 277-288, 1985.

*Primary Examiner*—Ronald W. Griffin

*Attorney, Agent, or Firm*—Oblon, Spivak, McClelland, Maier & Neustadt

[57] ABSTRACT

Compositions for anti-AIDS virus and other antivirus medicines are disclosed. Included are one having the ingredients other than glycyrrhizin contained in licorice, specifically flavonoids contained in licorice and more specifically not less than one kind of substance selected from a group consisting of liquiritigenin, i-liquiritigenin, liquiritin and i-liquiritin and glycyrrhizin produces allowed to contain not less than 3% of flavonoids contained in licorice based on glycyrrhizin as major constituting elements. Method of preparing said compositions having the filtrate obtained through the ultrafiltration of aqueous extract from licorice using ultrafiltration membrane with a fractionatable molecular weight of 10,000 to 100,000 as an effective ingredient and drugs for the pevention from infection and onset and for the therapy against AIDS used said compositions are also claimed.

5 Claims, No Drawings

COMPSITIONS FOR ANTIVIRUS MEDICINES

BACKGROUND OF THE INVENTION

The present invention relates to a composition and a drug, wherein flavonoids in the licorice are used for the antivirus agents, in particular, for the preventive therapy against AIDS [Acquired Immunodeficiency Syndrome] virus.

AIDS has become now a worldwide problem as a disease wherein said virus carriers amount presumably four million (end of the year 1987) and the mortality within two years after onset exceeds 70%. A feature of AIDS is that the T4 lymphocytes governing the immune system are destructed by AIDS virus resulting in the collapse of both of bacillary immunity and liquid immunity and finally the death comes from Karini's pneumonia, Kaposi's sarcoma, etc.

At the research organs in U.S.A. and other countries, the development of therapeutical drugs and onset-preventive drugs for AIDS is in haste, but, until today, only one kind of azidothymidine being of nucleic acid type is approved as a therapeutical drug for AIDS. However, even with said azidothymidine, the side-effects such as severe anemia, granulocytopenia, etc. are strong leaving a problem in the administration for a long term.

With glycyrrhizin being an effective ingredient of herbal medicine "licorice", the side-effect is hardly recognized. Thus, it is attracting the attention as an anti-AIDS agent permitting the long-term administration, but the anti-AIDS virus activity thereof is low and it has not been put into practice.

While, until today, any anti-AIDS virus active ingredient other than glycyrrhizin has not been found in the licorice, but, in said herbal medicine, triterpene glycosides such as glavaric acid etc., flavonoids such as liquiritin, i-liquiritin, liquiritigenin, i-liquiritigenin, glycyrol, licoricidin, etc. and physiologically active substances such as β-sitosterol, biotin, etc. are contained and the possibility of these ingredients to exhibit the anti-AIDS virus activity is also left behind. There, on the basis of knowledges and ideas aforementioned, whether or not there are substances which exhibit the antivirus activity (Newcastle Disease Virus, hereinafter referred to as NDV) except glycyrrhizin among the ingredients of licorice was first tested.

First, the tests for the anti-NDV activity of glycyrrhizin (content of glycyrrhizin: not less than 98%, hereinafter referred to as glycyrrhizin standard) and refined product of extract from licorice with aqueous ammonia (content of glycyrrhizin: 40%, hereinafter referred to as BS) was carried out in vitro. As a result, the anti-NDV activity was recognized for both, but BS showed the activity about ten times stronger and it became evident that there existed the antivirus active substances other than glycyrrhizin in the licorice.

Now, in order to clear up the substantiality of anti-NDV activity shown with BS, BS was fractionated in sequence by means of medium-pressure liquid chromatography and high-performance liquid chromatography to obtain a fraction (hereinafter referred to as BS-F) showing the activity scores times as strong as that of BS. This BS-F is yellow needle-like crystals and easily soluble into alcohol and ether and hardly soluble into water.

From these properties, BS-F was presumed to be a kind of flavonoids, and the identification test appearing in Japan Pharmacopeia, that is, the color identification test wherein BS-F is dissolved into ethanol and hydrochloric acid and magnesium are added was conducted. As a result, purplish red color was displayed showing the peculiar reaction of flavonoids.

Further, silica gel thin-layer chromatography (development solvent; acetone: benzene: i-amyl alcohol: water: 28% aqueous ammonia (10:3:3:1.5:0.5), coloring agent; acetic anhydride: sulfuric acid (3:1)) according to the method described in Japanese Patent Publication No. Sho 48-8458 and $^{13}C$-nuclear magnetic resonance spectrography were performed to identify BS-F being liquiritigenin. Besides, it should be noted supplementarilly that, also in infrared absorption spectrum, partial absorptions of flavonoid skeleton at 1660 $cm^{-1}$(>C═O) and 1240 $cm^{-1}$(C—O—C) were seen.

Based on the knowledges above, the anti-NDV activity tests were conducted similarly with licorice flavonoids other than liquiritigenin (liquiritin, i-liquiritin and i-liquiritigenin). At that time, all of the flavonoids were confirmed to have the anti-NDV activity, though weaker than that of liquiritigenin.

Further, the antivirus activity tests were performed replacing virus with Rous Sarcoma Virus (hereinafter referred to as RSV), which belongs to the same retrovirus family as AIDS virus does. As a result, the anti-RSV activity was seen with every flavonoid. In particular, liquiritigenin was confirmed to have strong activity. Thus, test against the AIDS virus, which is the final purpose of the present research, was conducted.

Consequently, all of the flavonoids inhibited the proliferation of AIDS virus. And yet, the proliferation-inhibitory effects shown therewith were made clear to be considerably stronger than that of glycyrrhizin, leading to the completion of the invention.

SUMMARY OF THE INVENTION

The invention provides the compositions for anti-AIDS virus and other antivirus medicines, which have the ingredients other than glycyrrhizin contained in licorice, specifically flavonoids contained in licorice and more specifically not less than one kind of substance selected from a group consisting of liquiritigenin, i-liquiritigenin, liquiritin and i-liquiritin and glycyrrhizin products allowed to contain not less than 3% of flavonoids contained in licorice based on glycyrrhizin as major constituting elements. Method of preparing said compositions having the filtrate obtained through the ultrafiltration of aqueous extract from licorice using ultrafiltration membrane with a fractionatable molecular weight of 10,000 to 100,000 as an effective ingredient is also described.

DETAILED DESCRIPTION OF THE INVENTION

The method of testing the antivirus activity in the invention will be shown below.

In the case of NDV, the cells made into a strain (Baby Hamster Kidney, hereinafter referred to as BHK) are first cultivated on a plate with 96 holes and NDV is added to infect by allowing to stand for about 30 minutes. Then, the samples diluted stepwise are added and, after 18 to 24 hours, which stage was the fusion between cells due to the infection by NDV inhibited at is judged under the microscope.

In the case of RSV, using first generation cultivated cells (Chick Embryo Fibroblast, hereinafter referred to as CEF), RSV is infected for about 30 minutes similarly to the case of NDV. Then, the samples diluted stepwise are added and, after 4 to 7 days, which stage was the transformation of cell due to the infection by RSV inhibited at is judged under the microscope.

The antivirus activity of respective ingredients in licorice of the invention was determined to obtain the results in Table 1 and 2.

TABLE 1

| Anti-NDV activity of licorice ingredients inhibitory concentration for the fusion of cells (mg/ml) | |
|---|---|
| Glycyrrhizin standard | 5-4 |
| BS (content of glycyrrhizin: 40%) | 0.4-0.3 |
| Liquiritigenin | 0.15-0.05 |
| i-Liquiritigenin | 0.15-0.05 |
| Liquiritin | 0.3-0.15 |
| i-Liquiritin | 0.3-0.15 |

TABLE 2

| Anti-RSV activity of licorice ingredients Inhibitory concentration for the transformation of cell (mg/ml) | |
|---|---|
| Glycyrrhizin standard | 1-0.5 |
| BS ( ) | 0.1-0.05 |
| Liquiritigenin | 0.008-0.004 |
| i-Liquiritigenin | 0.02-0.01 |
| Liquiritin | 0.02-0.01 |
| i-Liquiritin | 0.04-0.02 |

From these results, it became evident that the antivirus activity of flavonoids in licorice reached 15 to 100 times, averagely 30 times and 10 to 250 times, averagely 45 times as high as that of glycyrrhizin in the cases of NDV and RSV, respectively.

The compositions used in the invention include any one of liquiritigenin, i-liquiritigenin, liquiritin and i-liquiritin or the mixtures thereof and the coexistence of glycyrrhizin is not excluded.

When the aqueous extract of licorice is ultrafiltered using ultrafiltration membrans with a fractionatable molecular weight of 10,000 to 100,000, the filtrate thereof contains said ingredients and thus can be used.

The antivirus activity of glycyrrhizin is said to be due to the prevention from the adsorption of virus onto the surface layer of cells or the hindrance of protein kinase C existing in the cell walls.

Flavonoids are also presumed to hinder the kinase system, which is under further investigation.

In following, the invention is exemplified based on the examples, but it is not confined to these.

EXAMPLE 1

After passed 20 g of crude extract ingredients of licorice, which were obtained through the acidolysis of aqueous extract from the licorice roots, through an active charcoal column (volume: 100 ml), these were washed with water, dissolved out with 90% ethanol, and dried under reduced pressure to obtain about 10 g of fraction rich in flavonoids.

The antivirus effect of the fraction in NDV/BHK system proved to be 0.3 to 0.15 mg/ml in contrast with 0.4 to 0.3 mg/ml with the crude extract ingredients of licorice.

EXAMPLE 2

A mixture of 0.97 g of glycyrrhizin with 0.03 g of liquiritigenin and a mixture of 0.94 g of glycyrrhizin with 0.06 g of liquiritigenin were prepared to compare the antivirus property in NDV/BHK system with original glycyrrhizin.

| | |
|---|---|
| Glycyrrhizin | 5-4 mg/ml |
| Glycyrrhizin 0.97/liquiritigenin 0.03 | 4-2 mg/ml |
| Glycyrrhizin 0.94/liquiritigenin 0.06 | 2-1 mg/ml |
| Glucose 0.97/liquiritigenin 0.03 | 5-4 mg/ml |

In the cases of the formulations of not less than 3% of liquiritigenin to glycyrrhizin, the main ingredient having the antivirus property is considered evidently to be liquiritigenin.

EXAMPLE 3

Into 500 ml of water were dissolved 20 g of crude extract ingredients of licorice obtained through the acidolysis of aqueous extract from licorice roots, and, using an ultrafiltration membrane (UK-type, made by Toyo Filter Paper Co., Ltd., fractionatable molecular weight 10,000), ultrafiltration was performed under pressure of 3 kg/cm$^2$ to obtain 12 g of dried product through the concentration of the filtrate.

When testing the antivirus activity of this concentrate, the inhibitory concentration for the fusion of cells was shown to be 0.3 to 0.15 mg/ml.

As described, liquiritigenin, i-liquiritigenin, liquiritin and i-liquiritin, which are the flavonoid ingredients contained in the licorice, proved to have strong inhibitory effect against virus (AIDS virus) compared with glycyrrhizin, and it became evident that they could be used as preventive and therepeutical drugs for AIDS.

What is claimed is:

1. A pharmaceutical composition for the inhibition of viral proliferation, which comprises an effective amount of at least one substance selected from the group consisting of liquiritigenin, i-liquiritigenin, liquiritin and i-liquiritin, as a major constituting element; and a pharmaceutically acceptable excipient.

2. The pharmaceutical composition of claim 1, which comprises an effective amount of a filtrate obtained by ultrafiltering an aqueous extract of licorice using an ultrafiltration membrane having a fractionable molecular weight of 10,000 to 100,000, and a pharmaceutically acceptable excipient.

3. The pharmaceutical composition of claim 1, which further comprises glycyrrhizin as a major constituting element.

4. The pharmaceutical composition of claim 1, which inhibits the proliferation of Newcastle Disease Virus, Rous Sarcoma Virus and Acquired Immunodeficiency Syndrome Virus.

5. A method of preparing an active ingredient for the inhibition of viral proliferation, which comprises obtaining a filtrate by ultrafiltering an aqueous extract of licorice using an ultrafiltration membrane having a fractionable molecular weight of 10,000 to 100,000.

* * * * *